United States Patent
Porrata et al.

(10) Patent No.: US 7,182,741 B2
(45) Date of Patent: Feb. 27, 2007

(54) ADAPTABLE APPARATUS AND METHOD FOR TREATING CARPAL TUNNEL SYNDROME

(75) Inventors: Humberto Luis Porrata, Fort Lauderdale, FL (US); Alejandro Alberto Porrata, Miami, FL (US)

(73) Assignee: Porrata Group LLC

( * ) Notice: Subject to any disclaimer, the term of this patent is extended or adjusted under 35 U.S.C. 154(b) by 390 days.

(21) Appl. No.: 10/229,230

(22) Filed: Aug. 27, 2002

(65) Prior Publication Data
US 2003/0125652 A1    Jul. 3, 2003

Related U.S. Application Data

(60) Provisional application No. 60/315,087, filed on Aug. 27, 2001.

(51) Int. Cl.
*A61F 5/00*    (2006.01)
(52) U.S. Cl. .......................... 602/20; 602/21
(58) Field of Classification Search ............ 602/5, 602/13, 20–22; 128/877–879
See application file for complete search history.

(56) References Cited

U.S. PATENT DOCUMENTS

| | | | |
|---|---|---|---|
| 2,934,859 A | 7/1960 | Koski | |
| 4,382,439 A | 5/1983 | Shen | |
| 4,765,319 A | 8/1988 | Finnieston et al. | |
| 4,854,309 A | 8/1989 | Elsey | |
| 4,862,877 A * | 9/1989 | Barber ........................ | 602/22 |
| 4,899,763 A | 2/1990 | Sebastian | |
| 4,941,460 A | 7/1990 | Working | |
| 5,029,573 A | 7/1991 | Chow | |
| 5,152,302 A | 10/1992 | Fareed | |

(Continued)

FOREIGN PATENT DOCUMENTS

| | | |
|---|---|---|
| DE | 9200425 | 2/1991 |
| EP | 0 861 651 A1 | 2/1998 |
| FR | 2650175 | 12/1991 |
| WO | WO 97/23176 | 7/1997 |

*Primary Examiner*—Michael A. Brown
(74) *Attorney, Agent, or Firm*—Allan W. Watts; Daniel Crowe; Bryan Cave LLP (57) ABSTRACT

The apparatus of the present invention stretches the carpal ligament and the flexor retinaculum, as well as the superficial structures and muscles of the hand, in a safe manner under precise control of the patient or a healthcare professional. The preferred embodiment of the inventive apparatus includes a first housing with an open side portion adapted and configured to contact and retain the hypothenar region of the patient's hand, with a first edge of the first housing extending along a central longitudinal dorsal portion of the hand, and a second housing with an open side portion adapted and configured to contact and retain the thenar region of the patient's hand, with a second edge of the second housing also extending along a central longitudinal dorsal portion of the hand. A flexible resilient strap is secured to the first housing, and then wrapped around the second housing encompassing the thenar portion of the hand (i.e. around the thumb area), in such a manner as to pull the second housing (and thus the thenar portion of the hand) upward with the first and the second edges of the respective first and second housings serving as a fulcrum around which the hypothenar and thenar portions of the hand are bent. The strap is then secured to itself or to the first and/or the second housing to keep the hypothenar and thenar portions pulled apart during the course of treatment.

10 Claims, 8 Drawing Sheets

U.S. PATENT DOCUMENTS

| | | | | |
|---|---|---|---|---|
| 5,279,545 | A * | 1/1994 | Reese, Sr. .................... | 602/21 |
| 5,297,541 | A | 3/1994 | Hensey | |
| 5,427,577 | A | 6/1995 | Picchietti | |
| 5,584,854 | A | 12/1996 | Minarik | |
| 5,707,345 | A | 1/1998 | Fulk | |
| 5,810,753 | A | 9/1998 | Eberbach | |
| 5,897,549 | A | 4/1999 | Tankovich | |
| 5,916,185 | A | 6/1999 | Chitwood | |
| 5,916,187 | A | 6/1999 | Brill | |
| 5,925,007 | A | 7/1999 | Ashline | |
| 5,950,628 | A | 9/1999 | Dunfee | |
| 5,987,705 | A | 11/1999 | Reynolds | |
| 6,029,277 | A | 2/2000 | Picchione, II | |
| 6,120,472 | A * | 9/2000 | Singer, Jr. .................... | 602/64 |
| 6,146,347 | A * | 11/2000 | Porrata ........................ | 602/21 |
| 6,179,800 | B1 * | 1/2001 | Torrens ........................ | 602/21 |
| 6,200,286 | B1 | 3/2001 | Zamani | |
| 6,213,969 | B1 | 4/2001 | MacMorran et al. | |
| 6,217,536 | B1 * | 4/2001 | Gustafson .................... | 602/21 |
| 6,264,621 | B1 | 7/2001 | Paske | |
| 6,290,662 | B1 | 9/2001 | Morris et al. | |
| 5,438,726 | A1 | 7/2003 | Porrata | |
| 6,953,440 | B2 | 10/2005 | Porrata et al. | |
| 2002/0072786 | A1 | 6/2002 | Gordon | |
| 2003/0018286 | A1 | 1/2003 | Porrata | |
| 2003/0028136 | A1 | 2/2003 | Stager | |
| 2003/0125652 | A1 | 7/2003 | Porrata | |
| 2003/0125690 | A1 | 7/2003 | Porrata | |
| 2003/0125691 | A1 | 7/2003 | Porrata | |
| 2003/0130604 | A1 | 7/2003 | Porrata | |
| 2003/0130652 | A1 | 7/2003 | Porrata | |
| 2003/0130690 | A1 | 7/2003 | Porrata | |
| 2003/0130691 | A1 | 7/2003 | Porrata | |
| 2003/0130692 | A1 | 7/2003 | Porrata | |

* cited by examiner

ADAPTABLE APPARATUS AND METHOD FOR TREATING CARPAL TUNNEL SYNDROME

This application claims the benefit of U.S. Provisional Application Ser. No. 60/315,087, filed Aug. 27, 2001. This application is related to four concurrently filed co-pending patent applications, namely U.S. Ser. No. 10/228,395, entitled Non-Invasive Apparatus and Method for Treating Carpal Tunnel Syndrome, U.S. Ser. No. 10/228,739, entitled Adjustable Apparatus and Method for Treating Carpal Tunnel Syndrome, U.S. Ser. No. 10/228,899, entitled Automatic Apparatus and Method for Treating Carpal Tunnel Syndrome, U.S. Ser. No. 10/228,739, entitled Configurable Apparatus and Method for Treating Carpal Tunnel Syndrome, as well as co-pending patent application U.S. Ser. No. 10/199,747, entitled Apparatus and Method for Treating Carpal Tunnel Syndrome, filed Jul. 18, 2002, the contents of which are all hereby incorporated herein by reference.

FIELD OF THE INVENTION

This invention relates generally to treatment of carpal tunnel syndrome, and more particularly to a non-invasive apparatus and method for treatment of carpal tunnel syndrome.

BACKGROUND OF THE INVENTION

Carpal tunnel syndrome is a physiological disorder that afflicts over 850,000 people each year in the United States alone. In order to better understand the cause of the carpal tunnel syndrome and the difficulty in treating this serious disorder, a detailed explanation of the physiological factors and causes of carpal tunnel syndrome is presented below. Carpal tunnel syndrome is caused by a deleterious increase in pressure on the median nerve which passes through the carpal tunnel (or canal) in the hand, adjacent to the wrist. The deleterious increase in pressure, which is commonly brought on by prolonged repetitive motion of the hand and digits, is often caused by inflammation or damage to tendons for the hand which pass through the carpal tunnel along with the median nerve. Pressure increases can also be caused by narrowing of the carpal canal and by generalized swelling of the structures in the hand. Thus, when the carpal tunnel is narrowed from ligament shortening, muscle development or structural inflammation, the median nerve is undesirably compressed.

The carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones. The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical (invasive) and conservative (non-invasive). Surgical treatment consists of making an incision on the palmar aspect of the hand and splitting the carpal ligament, thus partially opening the carpal tunnel and relieving the pressure. This procedure, while occasionally successful, often has negative consequences, which include, but are not limited to, non-resolution of symptoms often requiring a second surgery, pain in the area of the scar, and injury to the superficial palmar branch of the median nerve causing persistent neurologic symptoms such as loss of full control over the hand. Furthermore, this procedure is very expensive. Understandably, surgical treatment is often considered as a last option.

Conservative, non-invasive treatment is typically separated into three categories—mild, moderate and alternative. Mild treatments may involve the use of anti-inflammatory medications, application of resting hand splints, physical therapy, modification of patient's activities that cause the condition, and even a change in the patient's job. Moderate treatments involve one or more mild treatments coupled with cortisteriod injections. Finally, alternative methods include acupuncture, massage, application of magnets, tai-chi exercises, and the like.

However, none of the above treatments have produced uniformly positive results. While some treatments may alleviate the symptoms of carpal tunnel syndrome in individual patients, the symptoms often return when the course of treatment is terminated. Furthermore, one of the main disadvantages of the various treatment approaches is that they must be delivered by a healthcare provider such as a physician or a physical or occupational therapist. This adds a significant level of inconvenience to the patient who must allocate time to visit the healthcare provider for injections and/or physical therapy. Medications that are used to provide relieve from the pain and discomfort caused by carpal tunnel syndrome also suffer from a number of disadvantages. For example, certain medications have undesirable side effects or interactions with the patient's other medications, if any.

As a result, a number of techniques for treating carpal tunnel syndrome that address at least some of the above problems have been developed over the years. Some merely maintain the patient's hand in a neutral position (such as the device disclosed in U.S. Pat. No. 5,014,689) to prevent the symptoms from worsening. Another approach involved mechanical stretching of the carpal ligament, as disclosed in U.S. Pat. No. 5,256,136. Yet another series of techniques advocated placement of a compression bracelet on the forearm (U.S. Pat. No. 5,441,058), or on the wrist (U.S. Pat. No. 5,468,220) to apply a predetermined pressure on certain portions of the forearm, or wrist, respectively, in order to widen the carpal tunnel and thus provide relief to the patient suffering from carpal tunnel syndrome.

However, the above-described previously known devices suffer from a crucial disadvantage. Application of pressure to different portions of the forearm and/or the wrist only has a minimal effect on widening the carpal tunnel, and may only provide temporary relief from carpal tunnel syndrome rather than eliminating or suppressing the condition.

Further development in the area of mechanical treatment of carpal tunnel syndrome continued, and eventually resulted in discovery of the Porrata principle, disclosed in the commonly assigned U.S. Pat. No. 6,146,347 to Humberto Porrata, that provides a novel and advantageous device and method for treating carpal tunnel syndrome that solve the problems posed by previously known devices and techniques. Most importantly, research conducted in conjunction with development of the Porrata device, has shown that carpal tunnel syndrome may be treated with great effectiveness by precise controlled transverse stretching of the carpal ligament and the flexor retinaculum. The U.S. Pat. No. 6,146,347 patent disclosed a splint-like device that fit over the patient's hand and a portion of the wrist. The device included rigid sections for contacting the thenar and hypothenar portions of the hand and a selectable active pressure source that, when actuated, applied pressure to the dorsal portion of the patient's hand opposed by the forces delivered by the thenar and hypothenar sections of the device in such a manner, as to transversely stretch the carpal ligament and the flexor retinaculum in a comfortable and controlled manner.

Nevertheless, the device of the U.S. Pat. No. 6,146,347 patent is susceptible to improvement. First, because of its construction it generally must to be fabricated in different sizes to fit various patients, and patients with unusual hand sized or shapes may need custom-fabricated devices. Second, it generally requires an active adjustable pressure source such as a bladder and pump combination for delivering pressure to the dorsal portion of the hand.

It would thus be desirable to provide an apparatus and method for treating carpal tunnel syndrome by stretching the carpal ligament and the flexor retinaculum of a patient's hand in a comfortable and controlled manner. It would further be desirable to provide an apparatus and method for treating carpal tunnel syndrome embodied in a device that is dynamically adaptable to patients of various physical characteristics. It would also be desirable to provide an apparatus and method for treating carpal tunnel syndrome embodied in a device that is easy and inexpensive to manufacture.

SUMMARY OF THE INVENTION

The apparatus and method of the present invention advantageously overcome the problems and drawbacks of previously known approaches for treating carpal tunnel syndrome. Similarly to the device disclosed in the commonly assigned U.S. Pat. No. 6,146,347 which is hereby incorporated by reference in its entirety, the main objective of the present invention is to apply the Porrata principle to stretch the carpal ligament and the flexor retinaculum, as well as the superficial structures and muscles of the hand, in a safe manner under precise control of the patient or a healthcare professional. However, the apparatus and method of the present invention enable the Porrata principle to be implemented in a device that may be readily used by patients with any size or shape hands. Furthermore, the inventive apparatus is very simple and inexpensive to manufacture.

Controlled and monitored use of the inventive apparatus dynamically treats carpal tunnel syndrome through the active application of pressure to large portions of the palm of the hand (in the thenar and hypothenar areas) while at the same time retaining and leveraging two portions of the central dorsum of the hand, in essence providing pressure in the opposite direction. This procedure stretches the carpal ligament, the flexor retinaculum, and superficial structures and muscles of the hand in the palmar aspect of the hand, in a readily, safely controllable and comfortable manner.

Considering that the constitutions of the carpal ligament and the flexor retinaculum are soft tissue composed of collagen and elastin, stretching the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

Various embodiments of the inventive apparatus commonly include a first housing with an open side portion adapted and configured to contact and retain the hypothenar region of the patient's hand with a first edge of the first housing extending along a central longitudinal dorsal portion of the hand, and a second housing with an open side portion adapted and configured to contact and retain the thenar region of the patient's hand with a second edge of the second housing also extending along a central longitudinal dorsal portion of the hand. A flexible resilient strap is secured to the first housing and then wrapped around the second housing encompassing the thenar portion of the hand (i.e. around the thumb area) in such a manner, as to pull the second housing (and thus the thenar portion of the hand) upward, with the first and the second edges of the respective first and second housings serving as a fulcrum around which the hypothenar and thenar portions of the hand are bent. The strap is then secured to itself or to the first and/or the second housing to keep the hypothenar and thenar portions pulled apart during the course of treatment.

Accordingly, the inventive apparatus is inexpensive and readily usable by any patient to prevent progression of carpal tunnel syndrome and to provide relief from symptoms by increasing the cross sectional area of the carpal tunnel, thus decreasing compression on the median nerve and decreasing the resulting symptoms.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote like elements throughout the several views.

DETAILED DESCRIPTION OF PREFERRED EMBODIMENTS

The present invention is described with reference to various materials that compose the inventive structures and elements thereof, and to various devices for selectively applying pressure to a specific area of the hand, by way of example only—it should be understood that the apparatus and method of the present invention may be utilized with any materials or selective pressure sources having properties similar to those described in the exemplary embodiments, without departing from the spirit of the invention.

The essence of the Porrata approach, disclosed and described in greater detail in the above-incorporated U.S. Pat. No. 6,146,347, involves applying pressure to a portion of the top surface of the hand (i.e., the central dorsal region), while at the same time applying opposing pressure to the thenar and hypothenar regions of the palm. The apparatus and method of the present invention advantageously implement the Porrata principle in a simple to use device that works equally well with different hand shapes and sizes.

Figure 1:
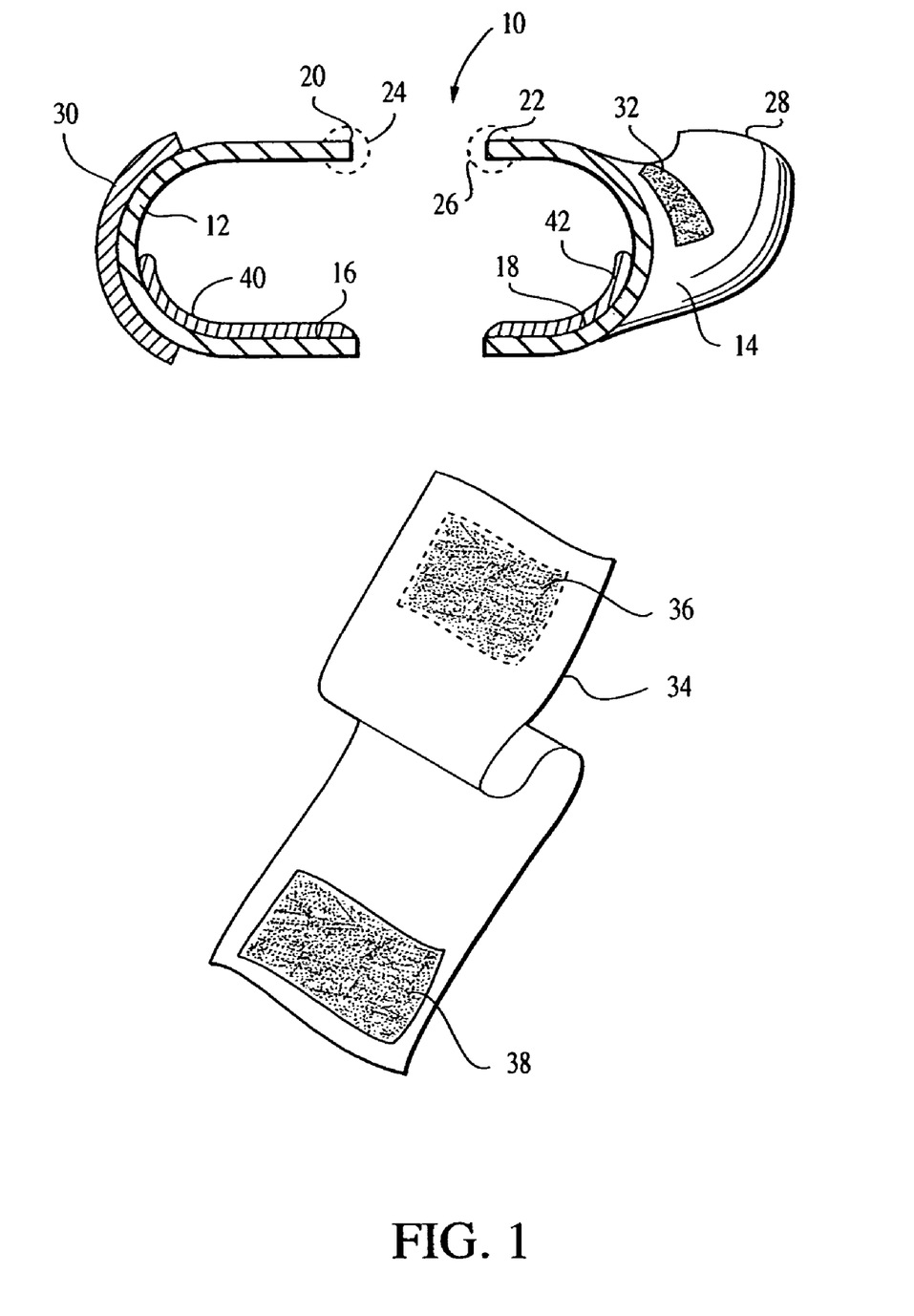
FIG. 1 is a cross section view of a first embodiment of the inventive apparatus for treating carpal tunnel syndrome.
Figure 2:
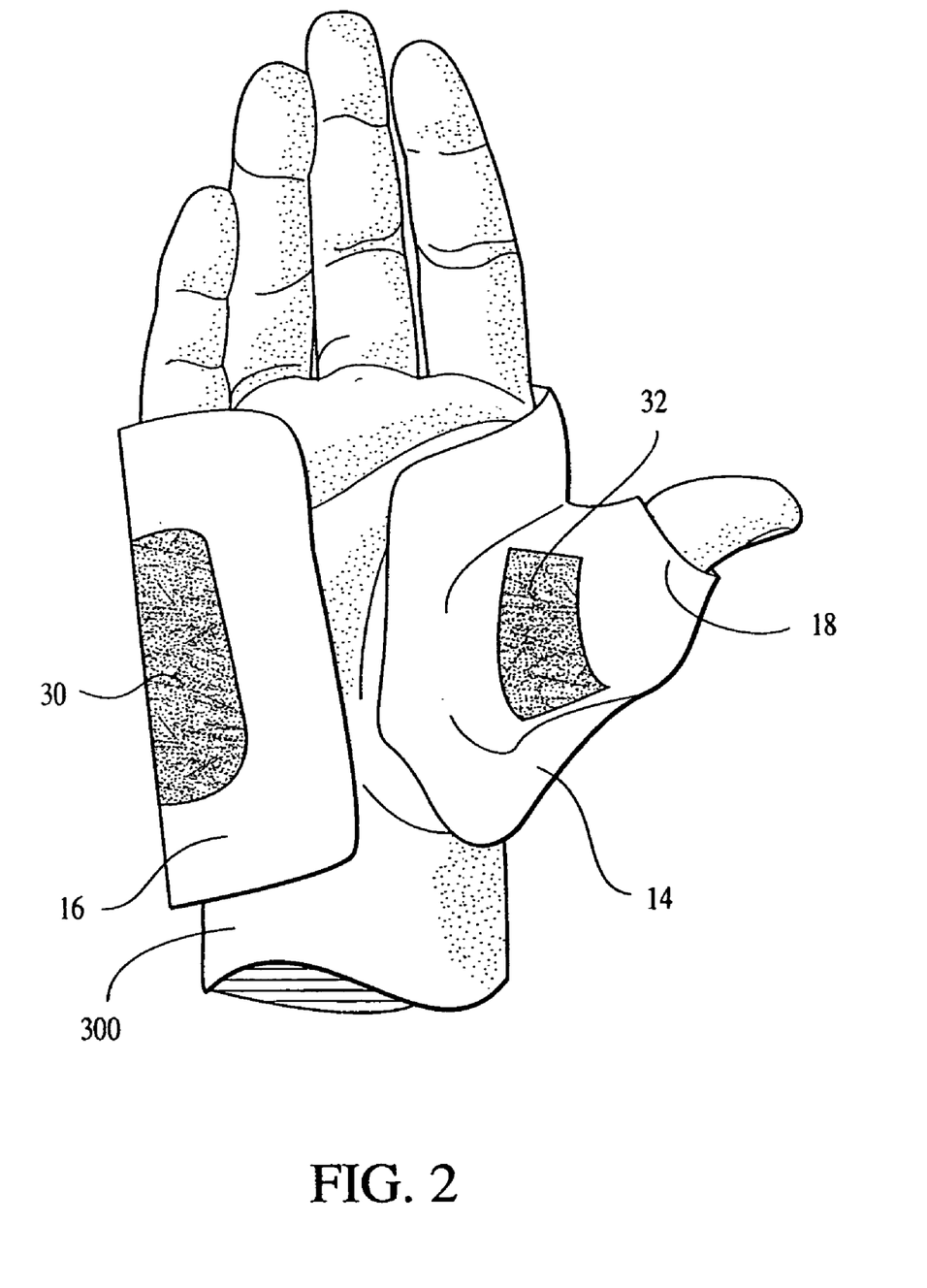
FIG. 2 is a bottom view of the first embodiment of the inventive apparatus for treating carpal tunnel syndrome of FIG. 1.

Referring now to FIGS. 1–2, a first embodiment of an inventive apparatus 10 is shown. The apparatus 10 includes a first housing 12 with a first support section 16 for retaining the hypothenar region of the hand, and a top first edge 20 disposed generally along the longitudinal central dorsal portion of the hand when the hand is inserted into the first housing 12, and a second housing 14 with a second support section 18 for retaining the thenar region of the hand, and a top second edge 22 disposed generally along the longitudinal central dorsal portion of the hand when the hand is inserted therein. The second housing 14 may comprise an optional thumb opening and support 28. The first and second housings 12, 14 may be composed of a rigid material such as metal, hard plastic or wood, or a resilient material such as fiberglass or resilient plastic, or a combination thereof. Optionally, the first and second housings 12, 14 may include a plurality of ventilation openings (not shown) to provide ventilation to the patient's hand during the operation of the apparatus 10. An optional first pressure element 24 may be disposed along the first edge 20, and an optional second pressure element 26 may be disposed along the second edge 22. The pressure elements 24, 26 may be composed of a resilient material and serve to improve the patient's comfort when the apparatus 10 is in use.

The apparatus 10 may also include an optional first resilient lining 40 along the inner surface of the first housing 12 and an optional second resilient lining 42 along the inner surface of the second housing 14. The linings 40, 42 may be composed of any resilient material including but not limited to: soft plastic, silicone gel, padding, foam, spring elements, and at least one fluid or air-filled bladder. Optionally, the linings 40, 42 may be disposed along the entire inner portions of the respective first and second housings 12, 14.

A first releasable connector 30 is disposed on an outer portion of the first housing 12, and a second releasable connector 32 is disposed on an outer portion of the second housing 14. A separate flexible resilient strap 34 is provided for use with the housings 12, 14. The strap 34 may be composed of any resilient material such as nylon webbing, leather, rubber, or any other synthetic or natural resilient flexible material. The strap 34 includes releasable attachment connectors 36, 38 (optionally only one such connector may be included but extended along the length of one or both of the surfaces of the strap 34), for releasable attachment to one or both of the first and second releasable connectors 30, 32. For example, the first and second connectors 30, 32 may be hook material, while connectors 36, 38 may be corresponding loop material. Optionally, the strap 34 may be permanently connected by one of its ends either to the first housing 12, or to the second housing 14.

Figure 3:
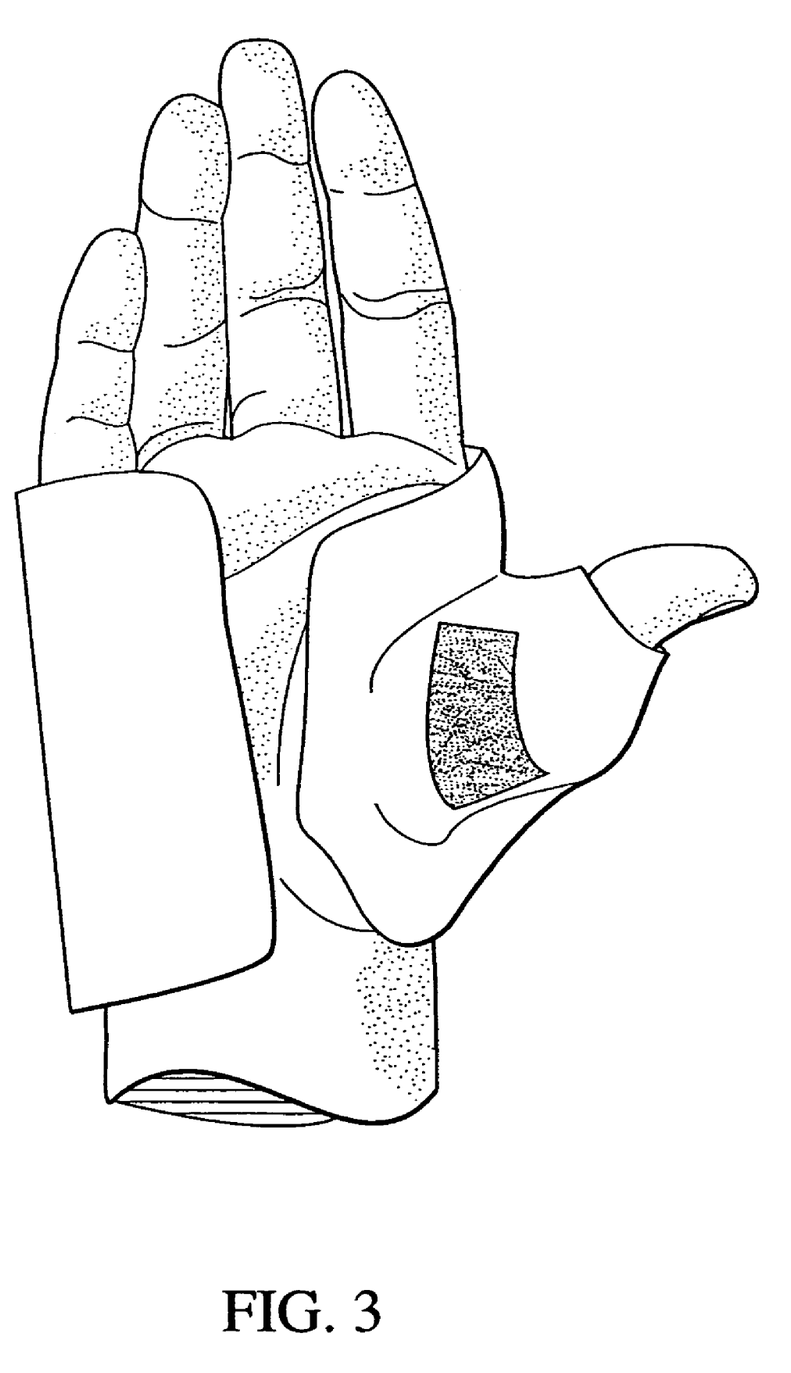
FIG. 3 is a bottom view of an exemplary implementation of the inventive apparatus for treating carpal tunnel syndrome of FIG. 1.
Figure 4:
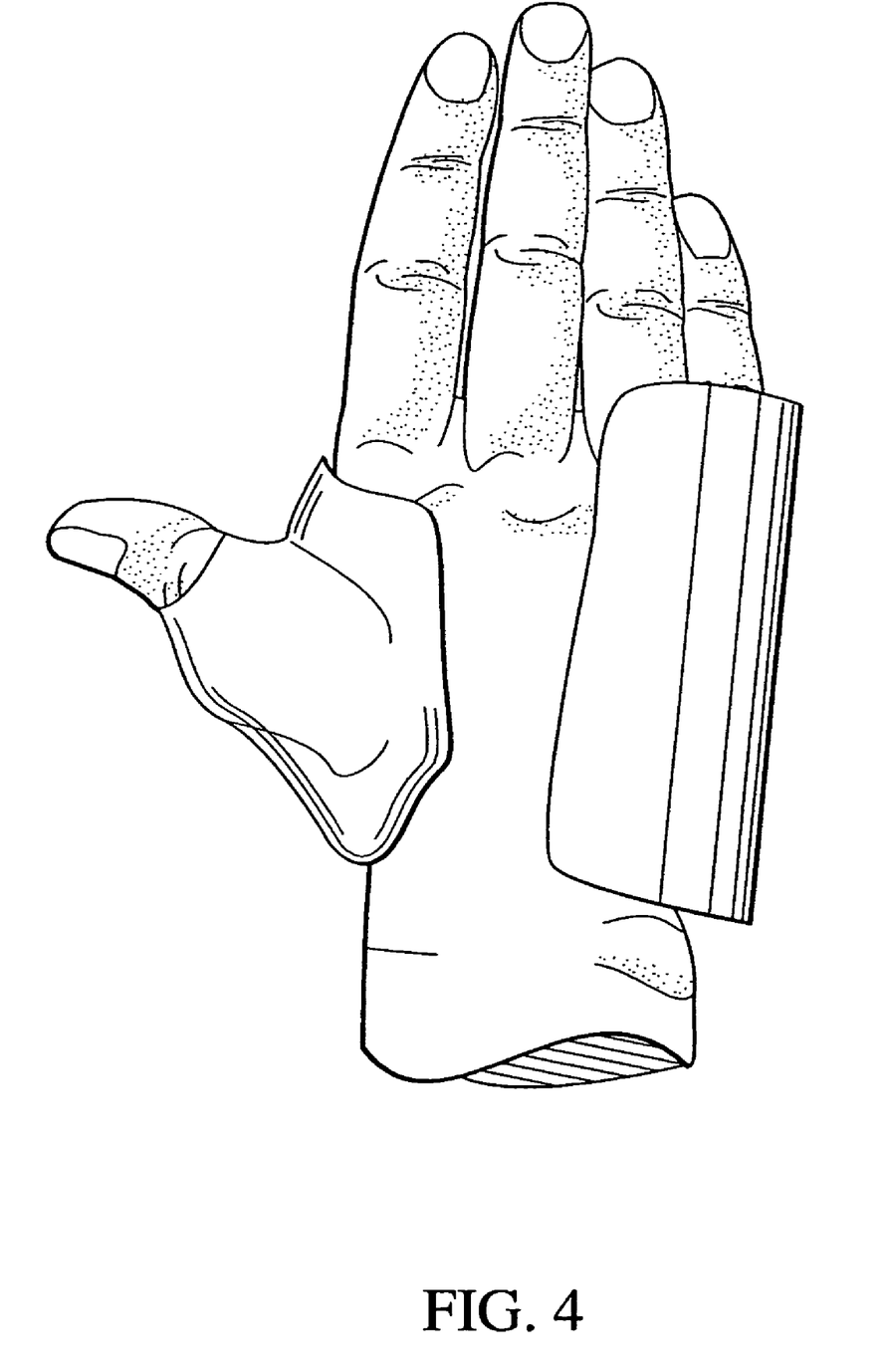
FIG. 4 is a top view of an exemplary implementation of the inventive apparatus for treating carpal tunnel syndrome of FIG. 1.
Figure 5:
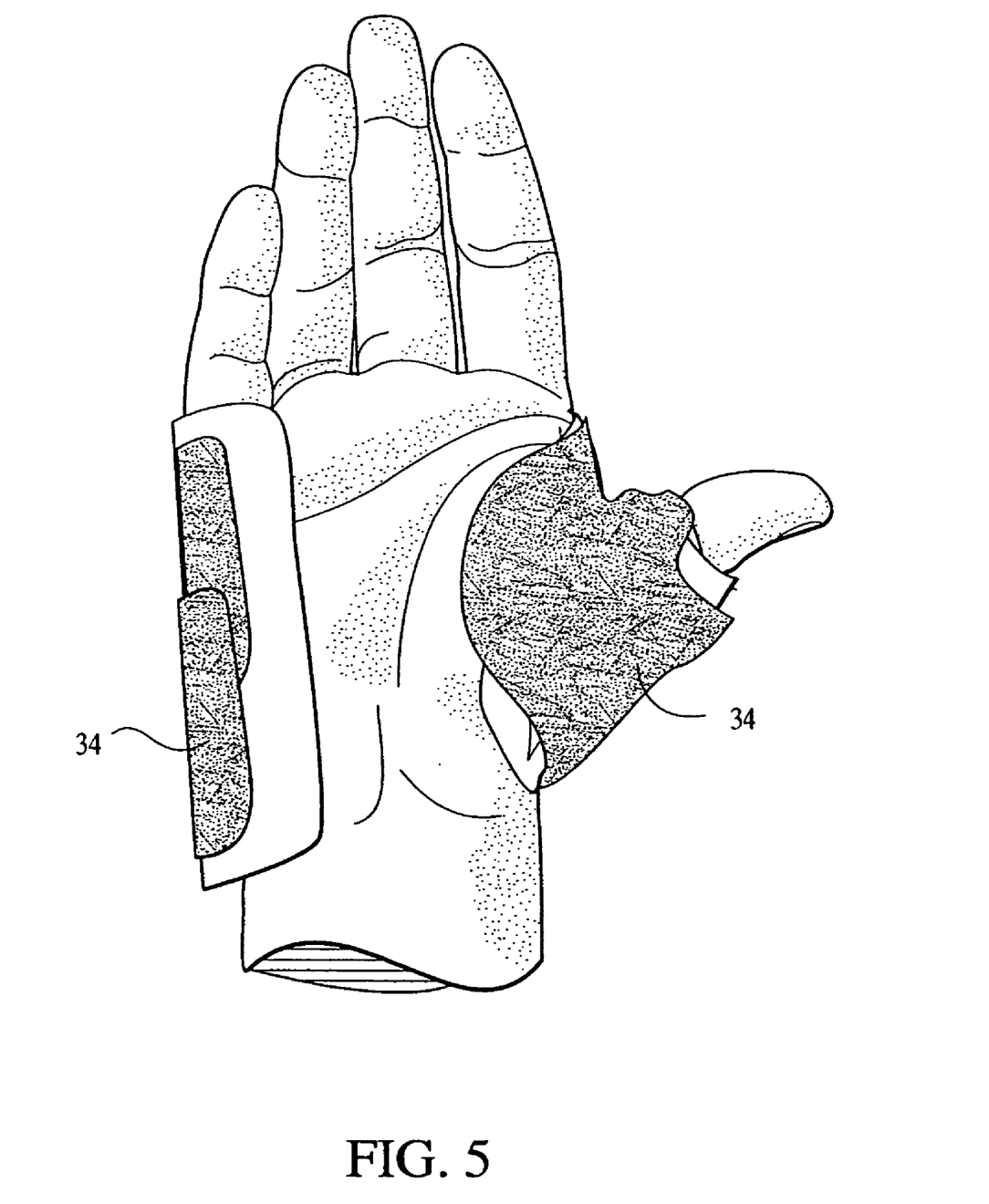
FIG. 5 is a bottom view of an exemplary implementation of the inventive apparatus for treating carpal tunnel syndrome of FIG. 1 during utilization by a patient.
Figure 6:
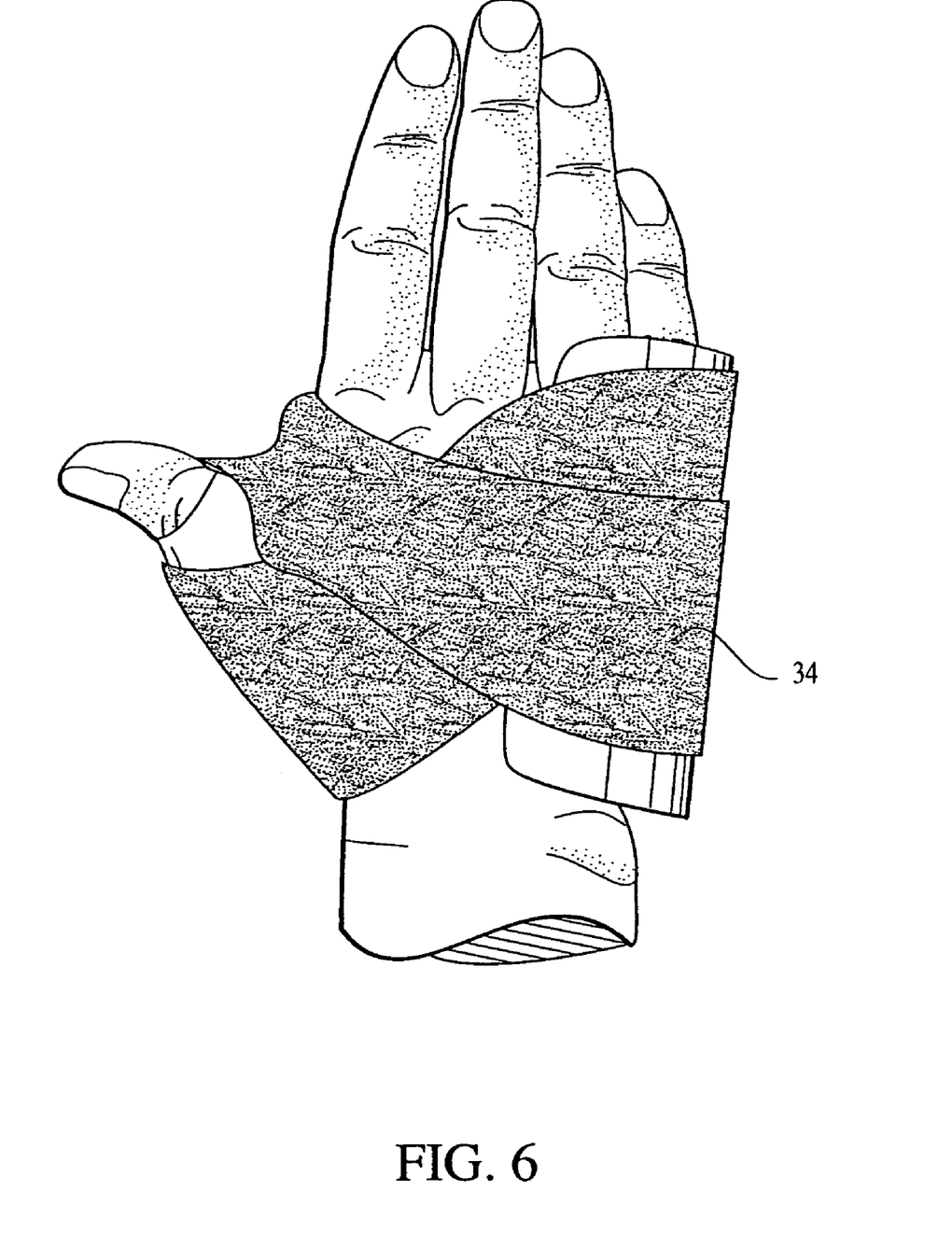
FIG. 6 is a top view of an exemplary implementation of the inventive apparatus for treating carpal tunnel syndrome of FIG. 1 during utilization by a patient.
Figure 7:
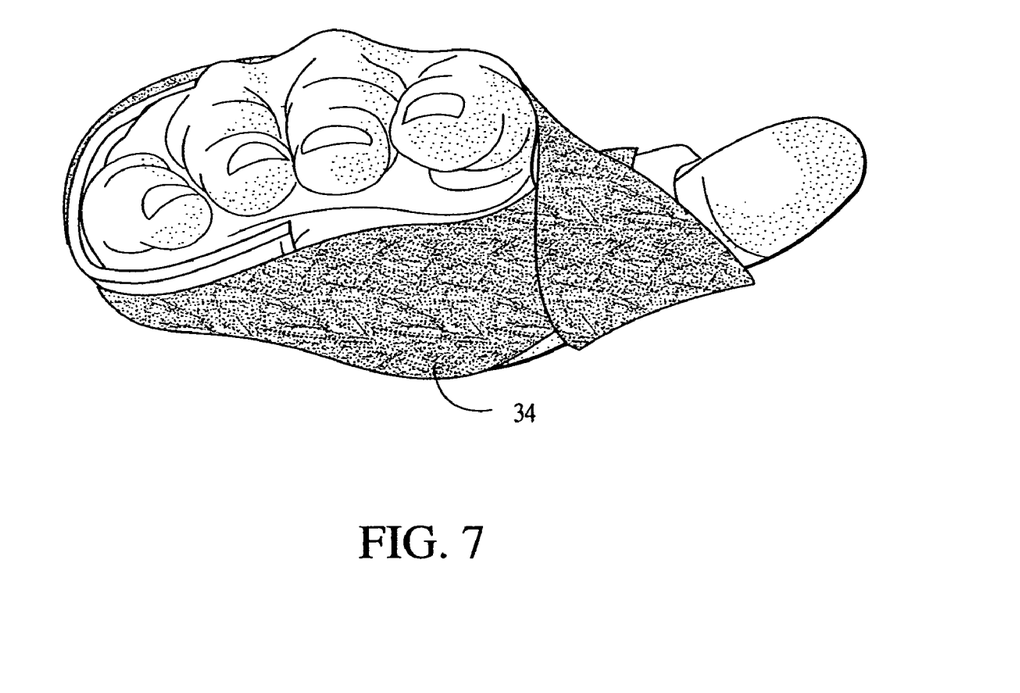
FIG. 7 is a front view of an exemplary implementation of the inventive apparatus for treating carpal tunnel syndrome of FIG. 1 during utilization by a patient.

Referring to FIGS. 3 and 4, to utilize the apparatus 10 for treatment, a person places their hand 300 into the first and second housings 12, 14, such that the hypothenar region of the palm contacts the first support section 16, the thenar region of the palm contacts the second support section 18, and the thumb extends through the thumb support 28. The first and second edges 20 and 22 are thus positioned along the central dorsal portion of the hand 300. Referring now to FIGS. 5–7, the strap 34 is then tightly wrapped around the second housing 14 and pulled towards the first and second edges 20 and 22 to create tension to exert a first upward force on the thenar region of the hand by the second support section 18 opposed by the downward force exerted by the first and second edges 20 and 22 on the central longitudinal dorsal region of the hand, and approximately parallel to a corresponding second upward force exerted by the first support section 16 on the hypothenar region of the hand. The strap 34 is then secured to the first housing 12 via at least one of the releasable connectors 36, 38 to maintain tension therein sufficient to maintain the first and second upward forces and the downward force, so as to implement the Porrata principle to widen the carpal canal and provide treatment of carpal tunnel syndrome to the patient.

Other tension-creating devices could be used to retain the first and second housings 12, 14 to apply a first upward force on the second housing 14 and thus on the thenar region of the hand through the second support section 18 and to apply a second upward force on the first housing 12 and thus on the hypothenar region of the hand through said first support section 16, wherein the first and the second upward forces are opposed by a downward force exerted by the first and the second edges 20, 22 on the central dorsal region of the hand so that the downward force is balanced, such that balanced and opposed action of the downward force and the first and second upward forces, causes carpal bones of the hand to separate to stretch a carpal ligament and a flexor retinaculum of the hand.

Figure 8:
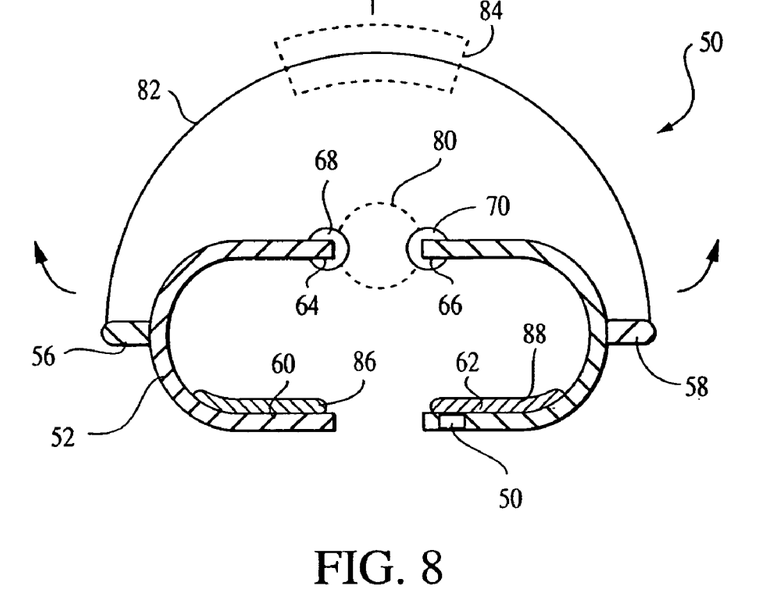
FIG. 8 is a cross section view of a second embodiment of the inventive apparatus for treating carpal tunnel syndrome.

Referring now to FIG. 8, a second embodiment of the inventive apparatus is shown as an apparatus 50. The apparatus 50 includes a first housing 52 with a first support section 60 for retaining the hypothenar region of the hand, and a top first edge 64 disposed generally along the longitudinal central dorsal portion of the hand, and a second housing 54 with a second support section 62 for retaining the thenar region of the hand, and a top second edge 66 disposed generally along the longitudinal central dorsal portion of the hand. The second housing 54 may comprise an optional thumb opening (not shown). The first and second housings 52, 54 may be composed of a rigid material such as metal, hard plastic or wood, or a resilient material such as fiberglass or resilient plastic, or a combination thereof. Optionally, the first and second housings 52, 54 may include a plurality of ventilation openings (not shown) to provide ventilation to the patient's hand during the operation of the apparatus 50. An optional first pressure element 68 may be disposed along the first edge 64, and an optional second pressure element 70 may be disposed along the second edge 66. The pressure elements 68, 70 may be composed of a resilient material and serve to improve the patient's comfort when the apparatus 50 is in use. Alternately, the apparatus 50 may comprise a fulcrum element 80 positioned along and attached to the first and second edges 64, 66 and configured such that the first and second housings 52, 54 can pivot upwardly around it. For example, the fulcrum element 80 may be a hinge.

The apparatus 50 may also include an optional first resilient lining 86 along the inner surface of the first housing 52, and an optional second resilient lining 88 along the inner surface of the second housing 54. The linings 86, 88 may be composed of any resilient material including, but not limited to: soft plastic, silicone gel, padding, foam, spring elements, and at least one fluid or air-filled bladder. Optionally, the linings 86, 88 may be disposed along the entire inner portions of the respective first and second housings 52, 54.

A first lever element 56 is disposed on, and perpendicular to, a substantially central outer portion of the first housing 52 and a second lever element 58 is disposed on, and perpendicular to, a substantially central outer portion of the second housing 54. An elongated line 82 preferably connects the first lever element 56 to the second lever element 58 and forms a general arc above the top portions of the first and second housings 52, 54. An optional handle 84 may be positioned along a central portion of line 82. Optionally, the line 82 may consist of two segments with the first segment connecting the first lever element 56 to one end of the handle 84, and the second segment connecting the second lever element 58 to the other end of the handle 84. The line 82 may be composed of any resilient, semi-rigid, or rigid material. For example, the line 82 may be composed of leather, rubber, synthetic or natural webbing, metal, or plastic. The handle 84 may also be composed of any of the above described materials or combinations thereof.

Figure 9:
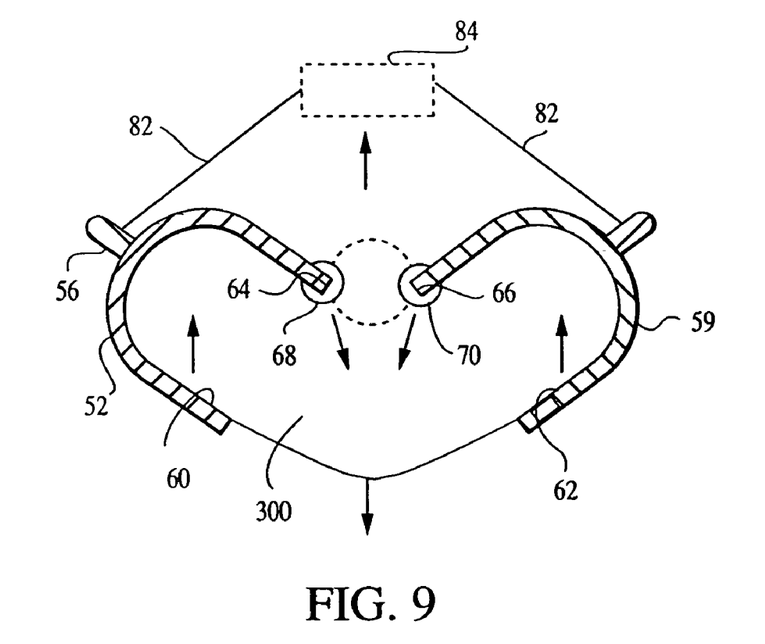
FIG. 9 is a cross-section view of the second embodiment of the inventive apparatus of FIG. 8 during utilization by a patient.

Referring now to FIG. 9, the operation of the apparatus 50 is shown. A person places their hand 300 into the first and second housings 52, 54, such that the hypothenar region of the palm contacts the first support section 60 and the thenar region of the palm contacts the second support section 62. The first and second edges 64 and 66 are thus positioned along the central dorsal portion of the hand 300. The line 82 (or the handle 84) is then pulled upwards while holding the hand 300 down (or while moving the hand 300 in the opposite direction). This exerts a first upward force on the thenar region of the hand by the second support section 62 and also exerts a second upward force on the hypothenar region of the hand by the first support section 60. These first and second upward forces are opposed by a downward force exerted by the first and second edges 64 and 66 on the central longitudinal dorsal region of the hand, so as to implement the Porrata principle to widen the carpal canal and provide treatment of carpal tunnel syndrome to the patient.

The apparatus 50 may also include an electronic device 70 that includes a laser or similar device adapted to specifically denature the proteins that make up the ligaments in the body, thus making it easier to stretch the ligaments. The electronic device 70 is preferably aligned with the flexor retinaculum or carpal ligament as the hand is placed in the apparatus 50. The electronic device 70 may also include conventional sensors to measure the amount of stretching of the flexor retinaculum or carpal ligament through, e.g., tension measurements or displacement of carpal bones. The laser and sensors may operate under computer control.

It should be noted that the individual elements shown in various embodiments of FIGS. 1–9 may be readily utilized in different embodiments or mixed without departing from the spirit of the invention. For example, the fulcrum element 80 of the apparatus 50 of FIG. 8, may be readily utilized in the apparatus 10 of FIG. 1. Furthermore, while cross sections of the various embodiment of the inventive apparatus are shown to be of semi-circular in shape, the cross section of the apparatus may comprise any other geometrical shape without departing from the spirit of the invention.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. An apparatus for treating carnal tunnel syndrome in a person's hand, the hand having a longitudinal axis, a palmar aspect with thenar and hypothenar regions, and a dorsal region opposed to the palmar aspect, the apparatus comprising a first housing having a first edge, a second housing having a second edge, a pressure element directly attached to and completely covering the first edge, a second pressure element directly attached to and completely covering the second edge, a first leveling element attached to the outer surface of the first housing, a second leveling element attached to the outer surface of the second housing, a fulcrum located between said first pressure element and said second pressure element, said fulcrum is located above and below said first and second pressure elements, said fulcrum being a pivot located between said first and second housing, an elongate means extending above said first and said second housing, said elongated means being attached at one end to said first leveling element and at the other end to said second leveling element.

2. The apparatus of claim 1, further comprising a first lining means attached to said first housing and a second lining means attached to said second housing.

3. The apparatus of claim 2, further comprising a handle attached to said elongated means.

4. The apparatus of claim 2, wherein the elongate means is a line that is made from the one of the group consisting of leather, rubbing or natural webbing.

5. The apparatus of claim 2, wherein the first and second linings are made of a resilient material.

6. The apparatus of claim 2, wherein the first and second housing having a gap located between them, said fulcrum permits said first housing to pivot away from said second housing making the gap between said first and said second housings larger.

7. A method of treating carpal tunnel syndrome in a person's hand, the hand having a longitudinal axis, a palmar aspect with thenar and hypothenar regions, and a dorsal region opposed to the palmar aspect, the method being performed using an apparatus comprising a first housing having a first edge, a second housing having a second edge, a pressure element directly attached to and completely covering the first edge, a second pressure element directly attached to and completely covering the second edge, a first leveling element attached to the outer surface of the first housing, a second leveling element attached to the outer surface of the second housing, a fulcrum located between said first pressure element and said second pressure element, said fulcrum is located above and below said first and second pressure elements, said fulcrum being a pivot located between said first and second housing, an elongate means extending above said first and said second housing, said elongated means being attached at one end to said first leveling element and at the other end to said second leveling element, the method including inserting the hand of a person into the first and second housing, so that the hypothenar region of the palm contacts a first support section and the thenar region of the of the palm contacts a second support section.

8. The method of claim 7 including the method step of positioning first and second edges along the central dorsal portion of the hand.

9. The method of claim 7 including the method step of exerting a first upward force on the thenar region of the hand using the second support section and exerting a second upward force on the hypothenar region of the hand using the first support section.

10. The method of claim 9, wherein the first and second upward forces are opposed by a downward force exerted by the first and second edges on the central longitudinal dorsal region of the hand to widen the carpal canal and provide treatment of carpal tunnel syndrome to the patient.

* * * * *